US008980882B2

(12) United States Patent
Roewer et al.

(10) Patent No.: US 8,980,882 B2
(45) Date of Patent: Mar. 17, 2015

(54) PHARMACEUTICAL PREPARATION COMPRISING PERMETHYLATED CYCLODEXTRIN

(76) Inventors: Norbert Roewer, Würzburg (DE); Jens Broscheit, Würzburg (DE)

(*) Notice: Subject to any disclaimer, the term of this patent is extended or adjusted under 35 U.S.C. 154(b) by 0 days.

(21) Appl. No.: 12/936,222

(22) PCT Filed: Apr. 1, 2009

(86) PCT No.: PCT/EP2009/002381
§ 371 (c)(1),
(2), (4) Date: Oct. 4, 2010

(87) PCT Pub. No.: WO2009/121585
PCT Pub. Date: Oct. 8, 2009

(65) Prior Publication Data
US 2011/0028457 A1    Feb. 3, 2011

(30) Foreign Application Priority Data

Apr. 4, 2008  (EP) .................................... 08006866

(51) Int. Cl.
| A61K 31/5517 | (2006.01) |
| A61K 31/724 | (2006.01) |
| A61K 9/00 | (2006.01) |
| A61K 31/05 | (2006.01) |
| A61K 31/715 | (2006.01) |

(52) U.S. Cl.
CPC ............... *A61K 9/0019* (2013.01); *A61K 9/006* (2013.01); *A61K 31/05* (2013.01); *A61K 31/715* (2013.01)
USPC ........................................... 514/220; 514/58

(58) Field of Classification Search
USPC .................................... 514/220, 58
See application file for complete search history.

(56) References Cited

U.S. PATENT DOCUMENTS

| 4,826,963 | A | * | 5/1989 | Stadler nee Szoke et al. .............................. 536/103 |
| 6,576,261 | B1 | | 6/2003 | Pitha |
| 6,699,849 | B1 | * | 3/2004 | Loftsson et al. ............... 514/58 |
| 2007/0093448 | A1 | * | 4/2007 | Westermann et al. .......... 514/58 |
| 2011/0015145 | A1 | * | 1/2011 | Bodor ............................. 514/46 |

FOREIGN PATENT DOCUMENTS

| EP | 1704858 | | 9/2006 |
| EP | 1704858 | A1 * | 9/2006 |
| JP | 1984-46228 | A | 3/1984 |
| JP | 2003-522207 | A | 7/2003 |
| JP | 2004-526730 | A | 9/2004 |
| JP | 2005-522422 | A | 7/2005 |
| WO | WO 9924073 | A1 * | 5/1999 |
| WO | 99/42211 | A1 | 8/1999 |
| WO | W001/30391 | | 5/2001 |
| WO | WO 0130391 | A2 * | 5/2001 |
| WO | 02/074200 | A1 | 9/2002 |
| WO | 03/063824 | A2 | 8/2003 |

OTHER PUBLICATIONS

Cyclobond® Handbook, A Guide to Using Cyclodextrin Bonded Phases for Chiral LC Separations, 6th ed., © 2002 Advanced Separation Technologies, Inc., p. 1-58, at p. 42-45.*
Armstrong et al., Separation of Drug Stereoisomers by the Formation of Beta-Cyclodextrin Inclusion Complexes, Science, vol. 232, p. 1132-1135, May 30, 1986.*
Braga et al. Inclusion of molybdenocene dichloride (CP2MoCl2) in 2-hydroxypropyl- and trimethyl-b-cyclodextrin: Structural and biological properties, Journal of Organometallic Chemistry 690 (2005) 2905-2912 ("Braga", of record).*
Loftsson, e.g., Brewster and Loftsson, Cyclodextrins as pharmaceutical solubilizers, Advanced Drug Delivery Reviews, 59 (2007) 645-666.*
Braga, et al. "Inclusion of molybdenocene dichloride (Cp2MoCl2) in 2-hydroxypropyl- and trimethyl-betacyclodextrin: Structural and biological properties" Journal of Organometallic Chemistry, Elsevier-Sequoia S.A. Lausanne, CH, vol. 690, No. 12, Jun. 15, 2005, pp. 2905-2912.
International Publication No. WO 99/42211, published Aug. 26, 1999 is the equivalent of JP 2003-522207 A, an English abstract is provided on the cover page of the publication.
International Publication No. WO 03/063824, published Aug. 7, 2003 is the English equivalent of JP 2005-522422 A.
International Publication No. WO 02/074200, published Sep. 26, 2002 is the English equivalent of JP 2004-526730 A.
English Abstract of JP 1984-46228 A, retrieved Jan. 21, 2014, 1 page.

* cited by examiner

*Primary Examiner* — Svetlana M Ivanova
(74) *Attorney, Agent, or Firm* — Casimir Jones S.C.

(57) ABSTRACT

The invention relates to a pharmaceutical preparation for applying a pharmaceutical agent. According to the invention, the preparation contains: a) a pharmaceutical agent which has an aromatic group or an aromatic part and the molecule of which has a maximum diameter of ≤2 nm; b) a permethylated cyclodextrin having a degree of substitution of 3 methyl groups per glucopyranose unit. The permethylated cyclodextrin and the pharmaceutical agent form a complex.

11 Claims, 1 Drawing Sheet

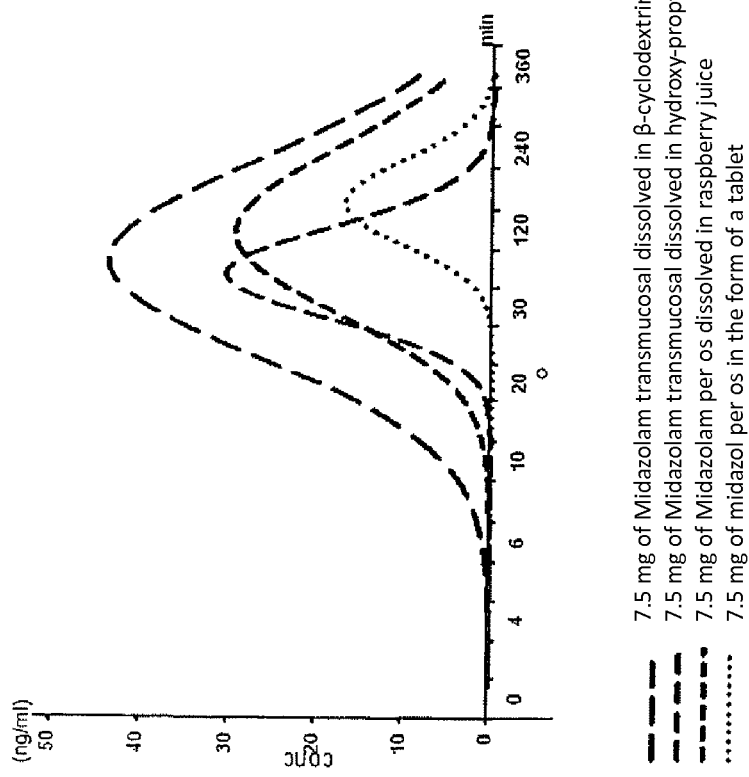

PHARMACEUTICAL PREPARATION COMPRISING PERMETHYLATED CYCLODEXTRIN

This application is a §371 US National Entry of International Application No. PCT/EP2009/002381, filed Apr. 1, 2009, which claims the benefit of European Application No. 08006866.1, filed Apr. 4, 2008.

The invention relates to a pharmaceutical preparation, for example preparations for reducing preoperative anxiety or for anesthetic purposes.

A frequent problem in pharmacy is to formulate a pharmaceutical active substance so that, using a specified method of administration, it is delivered in the desired concentration and as efficiently as possible to the intended site of action. Thus, an active substance intended for intravenous administration must to some extent be water-soluble, in order to attain a systemic concentration in the blood. On the other hand, as a rule it must possess a certain degree of lipophilicity, if it is to be able to penetrate at the intended site of action or through cell membranes. An active substance that only has good solubility in water may for example attain a high systemic concentration in the blood after intravenous administration, but if for example it has insufficient lipophilicity it will display low bioavailability, because at the intended site of action there may possibly be insufficient penetration through the cell membrane.

For certain methods of administration, for example transmucosal application, the bioavailability of an active substance may suffer because penetration through the mucosa is too slow or is delayed and therefore a sufficient systemic concentration of the active substance is not reached, or is reached too slowly. These problems will be clarified below for the example of so-called preoperative anxiolysis.

A patient regularly receives premedication prior to anesthesia and surgery. Its primary purpose is to reduce or prevent stress by means of so-called anxiolysis. According to relevant studies, a patient's preoperative mental state has a considerable influence on the intraoperative behavior of the circulation and the need for postoperative analgesics. Insufficient anxiolysis can for example lead to increased secretion of gastric acid with the risk of aspiration during induction of anesthesia. This can be life-threatening.

Benzodiazepines are regularly used for anxiolysis in the prior art.

Premedication on the day of surgery generally comprises oral administration of a short-acting benzodiazepine, in particular midazolam, about 45 to 60 min before starting anesthesia.

The bioavailability in oral application is very variable and therefore difficult to calculate. Incorrect dosage, possibly with inadequate anxiolysis, cannot be ruled out.

Furthermore, in oral administration, the accumulation time to reach a sufficient plasma level (45 to 60 min) is no longer compatible with the requirements on time management in hospitals. To achieve a high utilization rate of surgical equipment, a patient is commonly called to surgery with just 15 minutes' notice. This short notice does not allow sufficient anxiolysis through oral administration of benzodiazepines.

Formulation of midazolam with β-cyclodextrin to provide a solution for transmucosal application has already been proposed (WO-A-01/30391).

The invention is based on the task of creating a pharmaceutical preparation of the kind stated at the beginning, which permits safe and reliable application of an active substance with a profile of action that can be predicted sufficiently reliably.

According to the invention, it is envisaged that it contains:
a) a pharmaceutical active substance, which has an aromatic group or an aromatic moiety and for which the molecule has a maximum dimension of ≤2 nm;
b) a permethylated cyclodextrin with a degree of substitution of 3 methyl groups per glucopyranose unit;
wherein permethylated cyclodextrin and pharmaceutical active substance form a complex.

Cyclodextrins have already been proposed in the prior art (WO-A-01/30391) as excipients for complexing pharmaceutical active substances, optionally stabilizing them in aqueous solution or making them soluble and increasing their ability to pass through membranes.

DESCRIPTION OF THE DRAWING

FIG. 1 shows a graph depicting the variation in serum level of midazolam for the embodiment of the invention described and comparative examples.

The present invention has recognized that, surprisingly, special cyclodextrins, namely permethylated cyclodextrins with a degree of substitution of 3 methyl groups per glucopyranose unit, on the one hand permit very good stabilization and complexing even of lipophilic active substances in aqueous solution and on the other hand facilitate passage of the active substances through membranes.

Cyclodextrins generally have a toroidal shape and possess a correspondingly shaped cavity. The permethylated cyclodextrins used according to the invention have a number of advantageous properties, which on the one hand favor the complexing, and on the other hand the targeted release at the site of action, of the pharmaceutical active substances defined more precisely in claim 1. The complete absence of OH groups, which results from permethylation, promotes the entry of hydrophobic pharmaceutical active substances (aromatic group or aromatic moiety) into the cavity for the purpose of complexing. If methylation is incomplete, the entrances or edges of the cavity can be hydrophilic because of OH groups that are still present on the cyclodextrin and so make the complexing of hydrophobic active substances more difficult.

The invention has further recognized that residual OH groups that are present if methylation is incomplete can lead to an undesirable aggregation or agglomeration of cyclodextrin molecules in aqueous solution through formation of hydrogen bridging bonds. The use of permethylated cyclodextrins prevents this.

The pharmaceutical active substance to be complexed (guest molecule) must according to the invention have a maximum dimension of the molecule of 2 nm or less and must have an aromatic group or an aromatic moiety. This means that electron delocalization that is characteristic of aromatics occurs in at least one part of the guest molecule. The guest molecules therefore have a hydrophobic character and a suitable size for inclusion in the cyclodextrin cavity. Preferably the guest molecule does not have terminal hydrophilic groups, and preferably in particular does not have terminal OH groups.

According to the invention, a complex that is not aggregated/agglomerated, is water-soluble and is stable in aqueous solution, is formed, which can deliver pharmaceutical active substances quickly and reliably to the site of action. A possible explanation for the surprisingly improved action of the permethylated cyclodextrins could be that permethylated cyclodextrins have an increased lipophilic character and therefore facilitate interaction with the membrane and therefore the absorption of the cyclodextrin-complexed active substance.

The high lipophilicity of the cyclodextrins used according to the invention is reflected in a high log P value, which describes the distribution coefficient of the corresponding substance in the octanol/water solvent system. This log P value is, according to the invention, preferably at least 5, more preferably at least 7. A permethylated β-cyclodextrin has a log P value of 9.

Cyclodextrins have six (α-cyclodextrin), seven (β-cyclodextrin) or eight (γ-cyclodextrin) glucopyranose units. Each glucopyranose unit has three OH groups, which can be substituted, in the present case methylated. Permethylated cyclodextrin is fully substituted, i.e. the degree of substitution is 3.

Among the cyclodextrins, β-cyclodextrin is especially preferred.

The cyclodextrins used according to the invention have a polar outside surface and a hydrophobic cavity inside. They complex the preferably lipophilic pharmaceutical active substance and thus make it soluble in an aqueous medium. At the pharmacological site of action, the complex releases the active substance (possibly through "docking" of the cyclodextrin on the membrane), so that the membrane can be readily penetrated.

The uptake of medicinal products in target cells often takes place passively, because normally no transport systems across the cell membrane are available. The degree of passive flow of a medicinal product through a biological membrane by diffusion is largely determined by the lipophilicity of the medicinal product and its concentration gradient at the membrane. However, these two conditions are often in opposition. High lipophilicity (and thus good capacity for passive penetration of the cell membrane at the site of action) often means low water solubility, so that it is not possible for a large concentration gradient to develop across the membrane, which acts as a barrier, because the medicinal product in question has low solubility in the aqueous phase outside the cell membrane.

In the pharmaceutical preparation according to the invention, the preferably lipophilic pharmaceutical active substance is complexed by the cyclodextrin, so that as a complex it has good water solubility and can therefore be brought close to the membrane in higher concentration. Once it has been transported to the membrane, apparently it is released in a manner such that the lipophilic properties predominate during penetration of the membrane. With the preparation according to the invention, the complex thus makes it possible, owing to its water solubility, for a high concentration gradient to be established across the membrane barrier, and simultaneously the lipophilicity of the pharmaceutical active substance can produce a high penetration rate of the membrane barrier. The two factors for good penetration of a cell membrane at the pharmacological site of action, which as a rule are in opposition in the prior art, can thus, according to the invention, surprisingly be combined synergistically.

Preferably the complexing constant K of the complex of pharmaceutical active substance and cyclodextrin is between 10 and 70 l/mol, preferably 15 and 65 l/mol, more preferably between 20 and 55 l/mol, and especially preferably between 30 and 40 l/mol. Complexing constants in this range ensure sufficient stability of the complex in aqueous systems, but permit the release of the pharmaceutical active substance at the membrane of the intended site of action.

The pH of the pharmaceutical preparation according to the invention is preferably between 4 and 7, especially preferably between 5.5 and 6.5. This corresponds to the pH of the mucosae, so that for example transmucosal application is possible without irritation or other unpleasant side-effects.

The pharmaceutical preparation according to the invention can comprise various pharmaceutical active substances. It is preferable if the pharmaceutical active substance has a log P value of at least 3. This means that the common logarithm of the distribution equilibrium of this active substance in octanol/water mixtures is at least 3. It is therefore a measure of the lipophilicity of the pharmaceutical active substance. The log P values of the pharmaceutical active substances usable according to the invention can be very much higher, we may for example mention lipophilic substances such as halothane with a log P value of about 200.

Permethylated β-cyclodextrin possesses a cavity with a diameter of about 0.6 to 0.65 nm and a height of about 2 nm, which is suitable for receiving a pharmaceutical active substance. Therefore active substances that can fit this size of cavity are preferred.

As described above, a preparation according to the invention is therefore suitable for increasing the bioavailability of a pharmaceutical active substance at the intended site of action. In this mode of action, the complex of the preparation is delivered (for example via the bloodstream) to the pharmaceutical site of action, there the active substance is released from the complex and passes through the cell membrane. The cyclodextrin itself cannot penetrate the cell membrane.

According to another aspect of the invention, the preparation according to the invention can be used not only to ensure bioavailability by transporting the active substance (by means of the cyclodextrin complex) through the bloodstream to the site of action, but in certain methods of administration also makes it possible for the first time to establish a sufficiently high systemic concentration of the active substance that can also be predicted sufficiently reliably with respect to its profile over time. In this variant of the invention the complex of the preparation according to the invention does not release the active substance at the actual site of action, but improves, for example in transmucosal application, the passage of the active substance through the mucosal membrane, so that a specified systemic concentration of active substance is built up rapidly and predictably. Therefore in this variant of the invention the active substance is already released from the cyclodextrin complex on passage through the mucosal membrane.

The preparation according to the invention is therefore also suitable for a formulation for transmucosal application.

A pharmaceutical preparation for transmucosal application comprises a pharmaceutical active substance (optionally also several active substances) formulated with corresponding excipients, the active substance or substances being absorbed systemically completely or substantially through mucosae (in particular nasal and/or oral mucosae). Transmucosal application has the fundamental advantage that it permits faster, more reliable and more easily calculated systemic accumulation of an active substance, as the establishment of an appropriate serum level is not dependent on circumstances and imponderables of the gastrointestinal tract (first-pass effect due to passage through the liver after enteral absorption). The preparation according to the invention can be formulated in particular for transnasal, intralingual, intestinal or orovestibular application. Intestinal absorption can also benefit from this preparation.

The pharmaceutical active substance is especially preferably a benzodiazepine. The benzodiazepines can for example be selected from the group comprising alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam and loprazolam. Among these benzodiazepines, midazolam is especially preferred.

The proportion of the benzodiazepine in the pharmaceutical preparation can be, in a preferred embodiment, 0.5 to 2 wt. %, in particular 1 wt. %. The preparation is preferably an aqueous solution.

The invention further relates to the use of a permethylated cyclodextrin with a degree of substitution of 3 methyl groups per glucopyranose unit for the production of a pharmaceutical preparation, for example for transmucosal application. The use according to the invention is preferred, moreover, for the production of a medicinal product for preoperative anxiolysis.

According to another aspect of the invention, a pharmaceutical preparation according to the invention can be used to make an active substance that is insoluble or only sparingly soluble in water, accessible to intravenous administration. This will be explained for the example of propofol.

Propofol is an intravenous anesthetic that was tested in clinical practice for the first time in 1977. Solution of the anesthetic in a fat emulsion (trade name Diprivan®) was able to reduce the phlebalgia that is often observed in i.v. application, so that propofol was introduced into clinical practice in 1989.

This propofol lipid emulsion contains soybean oil, glycerol and egg phosphatides. Phlebalgia on injection has always been a common problem. Moreover, there can be serious allergic reactions. Since formulation as a fat emulsion promotes microbial growth, if the emulsion is contaminated, sepsis may develop after application even after short storage times.

According to the invention, a pharmaceutical active substance can be formed as a complex of cyclodextrin with the degree of methylation defined above and propofol, which does not have any of the aforementioned drawbacks.

As will be shown in the experimental section, a propofol formulation according to the invention has much lower equipotent doses compared with the lipid emulsion of the prior art. As no excipients are required for formulation of a lipid emulsion, the aforementioned problems of possible sepsis through microbial contamination also do not arise.

Examples of carrying out the invention are described below. FIG. 1 shows the variation in serum level of midazolam for the embodiment of the invention described and comparative examples.

EXAMPLE 1

Midazolam Preparation for Transmucosal Application

A 1% midazolam preparation for transnasal application is formulated as follows:

| | |
|---|---|
| Midazolam: | 10 mg |
| Permethylated β-cyclodextrin (degree of methylation: 3) | 150 mg |
| Hypromellose 400: | 1 mg |
| $H_3PO_4$, conc.: | 2.6 mg |
| NaOH 10%: | sufficient to give a pH of 4.2 |
| Potassium sorbate: | 1.4 mg |
| Water: | to 1 ml |

Hypromellose 400 is a hydroxypropyl methylcellulose with a molecular weight of about 400. It serves as a wetting agent for the mucosae. The pH of the resultant solution is 4.2.

In the present example the weight ratio of cyclodextrin to the pharmaceutical active substance is 15:1. Within the scope of the invention, ratios of cyclodextrin to pharmaceutical active substance from 50:1 to 10:1, especially 40:1 to 12:1, and more especially 20:1 to 12:1 are generally preferred.

In each case 0.75 ml of this solution (containing 7.5 mg of midazolam) was administered by transmucosal application to a group of five test subjects.

For comparison with the prior art, three further groups each of five test subjects were administered the same amount of active substance of 7.5 mg midazolam as follows:

COMPARATIVE EXAMPLE 1

The permethylated β-cyclodextrin of the example according to the invention was replaced with hydroxypropyl-β-cyclodextrin.

COMPARATIVE EXAMPLE 2

7.5 mg midazolam per os dissolved in raspberry juice.

COMPARATIVE EXAMPLE 3

7.5 mg midazolam per os in the form of a tablet.

For comparative example 1, apart from exchanging the cyclodextrins, the same recipe was used as in example 1.

The mean values of the variations in serum level of midazolam as a function of time after the respective application are shown in the diagram. It can be seen that the preparation according to the invention combines the fastest accumulation with attainment of the highest serum level and the longest time of action.

It was explained at the beginning that in hospitals patients are often called to surgery with only 15 minutes' notice. Therefore only this time window is available for anxiolytic premedication, because a short-acting benzodiazepine such as midazolam cannot be administered simply "on spec", without knowing when the operation will actually take place.

FIG. 1 shows that, after just 15 min, only the formulation according to the invention has built up a notable serum level, which already has an anxiolytic effect. All application forms of the prior art (including transmucosal application with hydroxypropyl-β-cyclodextrin as complexing agent) do not begin to build up a serum level until after 15 min. In practice this means that an anxiolytic premedication of the prior art hardly has any effect after just 15 min and therefore completely fails in its purpose.

EXAMPLE 2

Propofol Preparation for I.V. Application

Two 1% propofol formulations are made available. A lipid emulsion obtainable under the trade name Diprivan®, which contains 1% propofol in an emulsion base of soybean oil, glycerol and egg phosphatide, was made available as a formulation of the prior art.

Formulation according to the invention:

| | |
|---|---|
| Propofol: | 10 mg |
| Permethylated β-cyclodextrin: | 80.2 mg |
| $H_2PO_4$, conc.: | 2.6 mg |
| NaOH 10%: | sufficient to give a pH of 6.8 |
| Water: | to 1 ml |

This formulation will be designated hereinafter as CD-propofol.

Each of 12 Göttingen mini-pigs with a body weight between 48 and 53 kg were randomized and anesthetized with Diprivan® and CD-propofol. Administration was via a peripheral venous catheter.

The depth of anesthesia was monitored by cerebral state monitoring (CSM) and corresponding recording of the cerebral state index (CSI). A CSI of 40 to 60 was set as the desirable depth of anesthesia. Anesthesia was additionally monitored by recording an electrocardiogram (ECG), by pulse oxymetry (determination of the $SaO_2$ value) and capnometry (determination of the $pCO_2$ value).

The equipotent doses to achieve the aforementioned depth of anesthesia were 87.5±12.5 mg for the formulation according to the invention against 225±12.5 mg for the formulation of the prior art (Diprivan).

The formulation according to the invention shows much faster accumulation and decline. The formulation according to the invention starts to take effect 1 min after administration, whereas for the formulation of the prior art this time interval is 2 min. Action ceases with the formulation according to the invention after 19 min, and with the formulation of the prior art after 25.5 min. In contrast to the prior art, the formulation according to the invention does not give rise to any emulysis.

The invention claimed is:

1. A pharmaceutical preparation for the application of midazolam, wherein said pharmaceutical preparation contains:
   a) midazolam;
   b) a permethylated β-cyclodextrin with a degree of substitution of 3 methyl groups per glucopyranose unit;
   wherein the permethylated β-cyclodextrin and the midazolam form a complex.

2. The pharmaceutical preparation as claimed in claim 1 wherein said pharmaceutical preparation has a pH from 4 to 7.

3. The pharmaceutical preparation as claimed in claim 1, wherein the complexing constant K of the complex of midazolam and permethylated β-cyclodextrin is between 10 and 70 l/M.

4. The pharmaceutical preparation as claimed in claim 1, wherein the midazolam has a log P value of at least 3.

5. The pharmaceutical preparation as claimed in claim 1, wherein said pharmaceutical preparation is formulated for transmucosal application.

6. The pharmaceutical preparation as claimed in claim 5, wherein said pharmaceutical preparation is formulated for transnasal, intralingual, intestinal or orovestibular application.

7. The pharmaceutical preparation as claimed in claim 1, wherein the content of the midazolam is 0.5 to 2 wt. %.

8. The pharmaceutical preparation as claimed in claim 1, wherein said pharmaceutical preparation has a pH from 5.5 to 6.5.

9. The pharmaceutical preparation as claimed in claim 1, wherein the complexing constant K of the complex of pharmaceutical active substance and cyclodextrin is between 15 and 65 l/M.

10. The pharmaceutical preparation as claimed in claim 1, wherein the complexing constant K of the complex of midazolam and permethylated β-cyclodextrin is between 20 and 55 l/M.

11. The pharmaceutical preparation as claimed in claim 1, wherein the complexing constant K of the complex of midazolam and permethylated β-cyclodextrin is between 30 and 40 l/M.

* * * * *